(12) United States Patent
Hays et al.

(10) Patent No.: US 10,667,880 B2
(45) Date of Patent: Jun. 2, 2020

(54) TRAY FOR TEMPORARY STORAGE OF CATHETERS AND OTHER COILED SURGICAL DEVICES

(71) Applicant: Ahn Surgical Innovation, LLC, Dallas, TX (US)

(72) Inventors: Kimberly Ahn Hays, Dallas, TX (US); Sam S. Ahn, Dallas, TX (US)

(73) Assignee: AHN SURGICAL INNOVATION, LLC, Dallas, TX (US)

( * ) Notice: Subject to any disclaimer, the term of this patent is extended or adjusted under 35 U.S.C. 154(b) by 0 days.

(21) Appl. No.: 16/125,127

(22) Filed: Sep. 7, 2018

(65) Prior Publication Data

US 2019/0076207 A1    Mar. 14, 2019

Related U.S. Application Data

(60) Provisional application No. 62/555,819, filed on Sep. 8, 2017.

(51) Int. Cl.
*A61B 50/33* (2016.01)
*A61B 50/20* (2016.01)
(Continued)

(52) U.S. Cl.
CPC ........ *A61B 50/33* (2016.02); *A61B 17/06061* (2013.01); *A61B 50/20* (2016.02);
(Continued)

(58) Field of Classification Search
CPC ... A61B 17/06; A61B 17/06061; A61B 19/02; A61B 50/20; A61B 50/22; A61B 50/30;
(Continued)

(56) References Cited

U.S. PATENT DOCUMENTS

| 4,925,448 A | 5/1990 | Bazaral |
| 5,125,416 A | 6/1992 | Phillips |

(Continued)

FOREIGN PATENT DOCUMENTS

| EP | 1616593 A1 | 1/2006 |
| WO | 20160196785 A1 | 12/2016 |

OTHER PUBLICATIONS

International Search Report and Written Opinion issued in corresponding International Application No. PCT/US2018/049999, dated Mar. 6, 2019, 16 pages.

*Primary Examiner* — Bryon P Gehman
(74) *Attorney, Agent, or Firm* — Snyder, Clark, Lesch & Chung, LLP

(57) ABSTRACT

A storage tray provides storage for multiple types of wires, catheters, and other instruments used during surgical procedures. The storage tray includes a base and a set of walls forming a basin that holds liquid. A wire containment section within the basin holds multiple coiled guidewires in a wire channel filled with the liquid. The wire containment section includes an inner wall and one or more wall segments forming an outer boundary of the wire channel. Flaps extend orthogonally from the walls and over portions of the wire channel to prevent the guidewire from springing out of the wire channel. A wire holder outside the wire channel holds end portions of the guidewires. Pulling an end portion of one of the coiled guidewires horizontally causes the guidewire to slide along the inner wall for separation and removal from the storage tray.

20 Claims, 15 Drawing Sheets

(51) Int. Cl.
*A61M 25/09* (2006.01)
*A61B 50/30* (2016.01)
*A61B 50/22* (2016.01)
*A61B 17/06* (2006.01)
*A61M 25/00* (2006.01)
*A61B 50/00* (2016.01)
*A61B 50/36* (2016.01)

(52) U.S. Cl.
CPC .............. *A61B 50/22* (2016.02); *A61B 50/30* (2016.02); *A61M 25/002* (2013.01); *A61M 25/09* (2013.01); *A61B 50/36* (2016.02); *A61B 2050/005* (2016.02); *A61B 2050/3005* (2016.02); *A61B 2050/3008* (2016.02)

(58) Field of Classification Search
CPC ... A61B 50/33; A61B 50/36; A61B 2050/005; A61B 2050/3005; A61M 25/00; A61M 25/002; A61M 25/09
USPC .......................................... 206/210, 363, 364
See application file for complete search history.

(56) References Cited

U.S. PATENT DOCUMENTS

| | | | |
|---|---|---|---|
| 5,738,213 A | 4/1998 | Whiting et al. | |
| 5,769,222 A | 6/1998 | Banerian | |
| D433,130 S | 10/2000 | Cude et al. | |
| 6,547,072 B2* | 4/2003 | Whiting .............. | A61M 25/002 206/210 |
| 6,569,106 B1 | 5/2003 | Ullman | |
| 7,490,722 B2* | 2/2009 | Mayda, II .......... | A61M 25/002 206/364 |
| 9,022,212 B2* | 5/2015 | Spaargaren ........ | A61M 25/002 206/364 |
| 9,744,333 B2* | 8/2017 | Terzibashian ....... | A61M 25/002 |
| 2003/0141407 A1 | 7/2003 | Dannecker et al. | |
| 2006/0260968 A1 | 11/2006 | Mayda, II et al. | |
| 2009/0071851 A1 | 3/2009 | Maki et al. | |
| 2012/0312703 A1 | 12/2012 | Koellhofer et al. | |
| 2014/0110296 A1* | 4/2014 | Terzibashian ....... | A61M 25/002 206/438 |
| 2014/0374295 A1 | 12/2014 | Lessne | |
| 2018/0250495 A1* | 9/2018 | McNabb ............. | A61M 25/002 |

\* cited by examiner

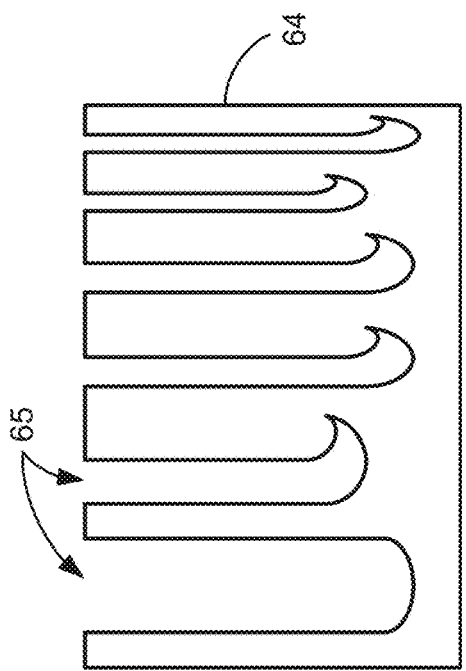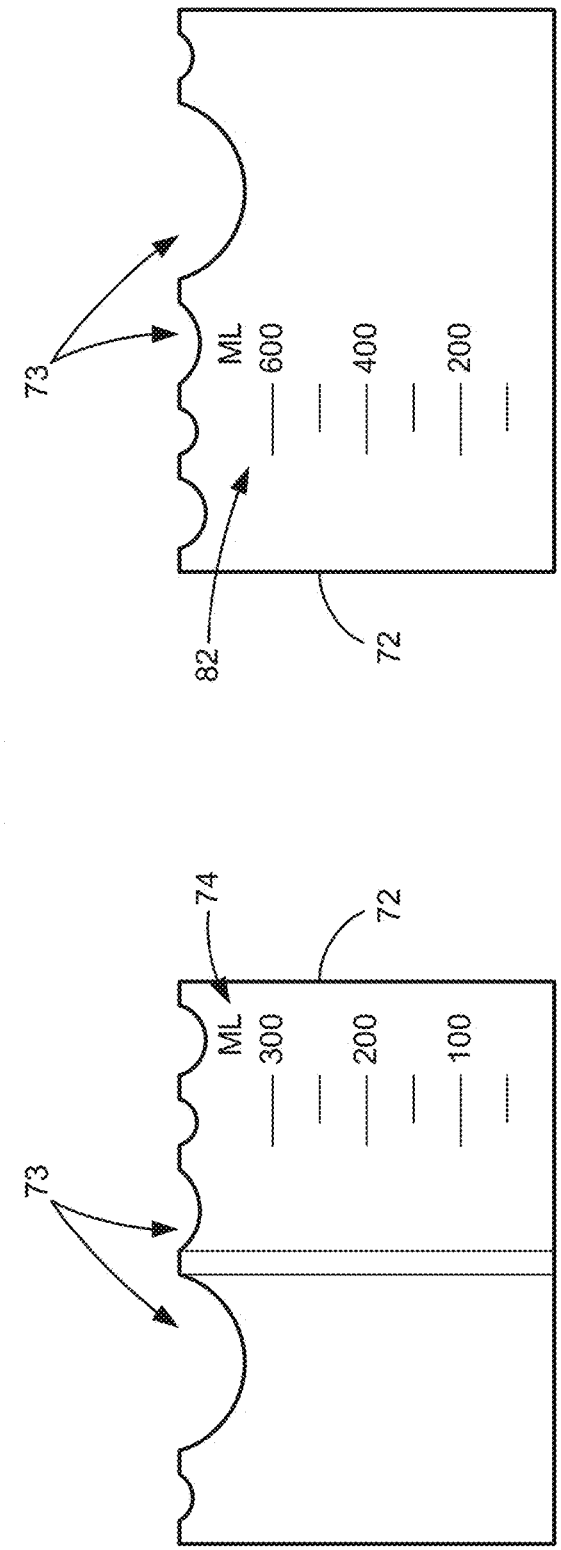

TRAY FOR TEMPORARY STORAGE OF CATHETERS AND OTHER COILED SURGICAL DEVICES

CROSS-REFERENCE TO RELATED APPLICATION

The application claims priority from U.S. Provisional Patent Application No. 62/555,819, filed Sep. 8, 2017, the contents of which are hereby incorporated herein by reference in its entirety.

BACKGROUND OF THE INVENTION

Endovascular procedures have become the preferred method of intervention for patients with vascular and cardiovascular disease. These procedures allow lower complications rates and quicker recovery times because instead of making a large incision, only a small puncture, typically through the groin, is required for access. Guidewires, catheters, and interventional devices such as balloons and stents are then threaded through this puncture and guided through different blood vessels to access and treat the patient.

Guidewires are used to direct a catheter to an identified site within a cardiovascular or peripheral vascular system of a patient for the purpose of diagnosis and/or treatment. Catheters are used for administration of fluid, such a saline, contrast, or therapeutic agents, at the identified site. The guidewire is typically placed into a blood vessel of the patient and is directed by a medical practitioner to the identified site of the patient's body. A catheter is then advanced over the guidewire until the functional structure of the catheter is located in proximity of the identified site.

Different sizes/gages of guidewires and different sizes of catheters may be used during a surgical procedure for different applications. Thus, multiple guidewires, catheters and other devices are typically laid out for access during a surgical procedure. Management of guidewires, catheters, and interventional devices during surgical procedures can become an unwanted distraction. Used guidewires or catheters have conventionally been coiled up manually and held down on an operating table with wet towels, held in a water basin, simply placed on the operating table, or sometimes fall to the floor after being used.

BRIEF DESCRIPTION OF THE DRAWINGS

FIG. 5 is an end view of a catheter/instrument holders for the catheter channel of FIG. 2A;

FIGS. 6A and 6B are front and rear end views of a wall section for the saline solution compartment of FIG. 2A;

DETAILED DESCRIPTION OF THE PREFERRED EMBODIMENTS

Figure 1:
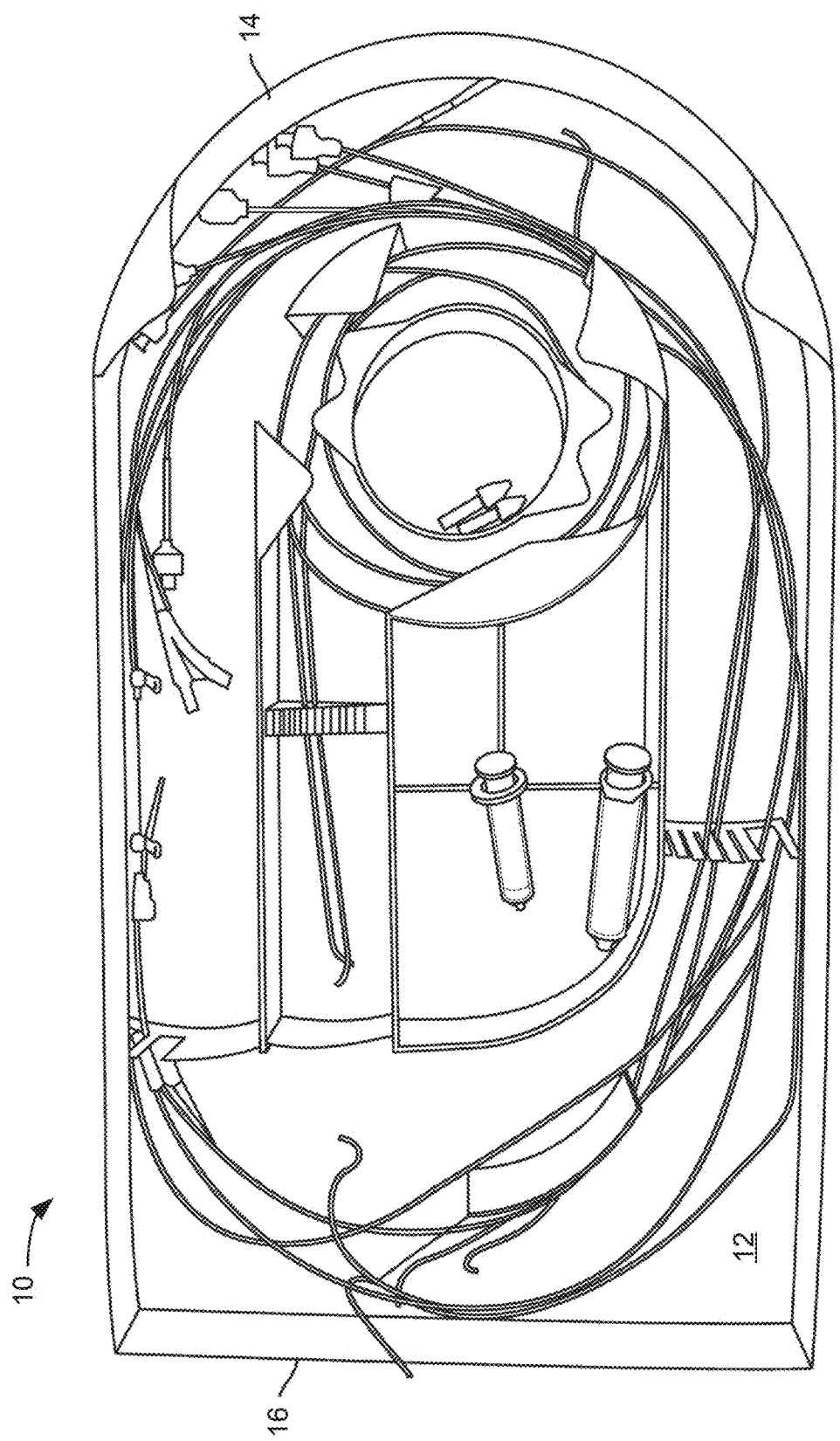
FIG. 1 is a top perspective view of a storage tray loaded with surgical instruments, according to an implementation described herein.

The following detailed description refers to the accompanying drawings. The same reference numbers in different drawings may identify the same or similar elements.

The present invention relates to a device to contain guidewires, catheters, and other devices used in surgical procedures. These surgical procedures can be vascular, endovascular, cardiology, urology, and other surgeries that involve guidewire and/or catheter use. In one implementation, the present invention is directed to a disposable holder for storage and retrieval of coiled medical guidewires (or simply "wires") and catheters, wherein the holder facilitates the storage and extraction of the coiled guidewires and catheters from the holder.

In order to navigate to lesions or other areas requiring medical attention in all parts of the body, numerous devices of varying quantity and lengths must be used within one procedure. For example, to treat the farthest-most vessel in the lower extremity, an introducer guidewire, a stiff wire, a glide-wire, balloons of varying sizes, one or more catheters with varying tips, and possibly a stent might all be used in one procedure. Each of these items may be at least 18 inches (about 45 centimeters) and up to 118 inches (about 300 centimeters) in length. Furthermore, newly developed wires and catheters may become longer in the near future, as different access points (e.g., apart from the groin) are beginning to be used in surgical procedures. These items are typically kept sterile by manually winding each one into a circle and holding down the ends with the weight of wet gauze. At times, these items are re-threaded back in their original housing. An additional complication is that after being taken out of their original packaging, these items often look very similar A scrub technician is typically responsible for organizing, tracking, and keeping these items sterile throughout the procedure, which can prove to be a difficult task, especially during complicated procedures that require a high number of disposable endovascular devices. Thus, there remains a need for an efficient way to organize and manage multiple items in a surgical environment.

According to an implementation, a storage tray provides storage for multiple types of wires, catheters, and other instruments used during surgical procedures. The storage tray may include a substantially flat horizontal base and a set of vertical walls forming a basin that holds liquid. A wire containment section within the basin may hold multiple coiled guidewires in a wire channel filled with the liquid. The wire containment section may include an inner wall and a group of non-contiguous wall segments forming an outer boundary of the wire channel. Flaps may extend orthogonally from the walls and over portions of the wire channel to prevent the guidewire from springing out of the wire channel. A wire holder outside the wire channel holds end portions of the guidewires. Pulling an end portion of one of the coiled guidewires horizontally causes the guidewire to slide along the inner wall for separation and removal from the storage tray.

According to another implementation, a method for using the storage tray for surgical procedures is provided. The method may include adding liquid into the basin of the storage tray, inserting multiple coiled guidewires past the flaps into the wire channel so that the coiled guidewires expand against the group of non-contiguous wall segments, and inserting an end portion of each of the multiple coiled guidewires into different slots of the wire holder. The method further includes selecting, as a selected guidewire, one of the multiple coiled guidewires for use during a surgical procedure; removing the end portion of the selected guidewire from the wire holder; and pulling the end portion of the selected guidewire horizontally until the selected guidewire exits the wire channel.

FIGS. 1-6B provide diagrams of exemplary views of a storage tray 10 (also referred to herein as a "device") according to implementations described herein. More particularly, FIG. 1 is a top perspective view of storage tray 10, loaded with surgical instruments in an exemplary implementation. FIGS. 2A and 2B are top and side views, respectively, of storage tray 10, according to another implementation. FIG. 2C is a cross-sectional view of storage tray 10 along line A-A of FIG. 2A. FIGS. 3-6B provide enlarged views of different portions of storage tray 10.

Figure 2A:
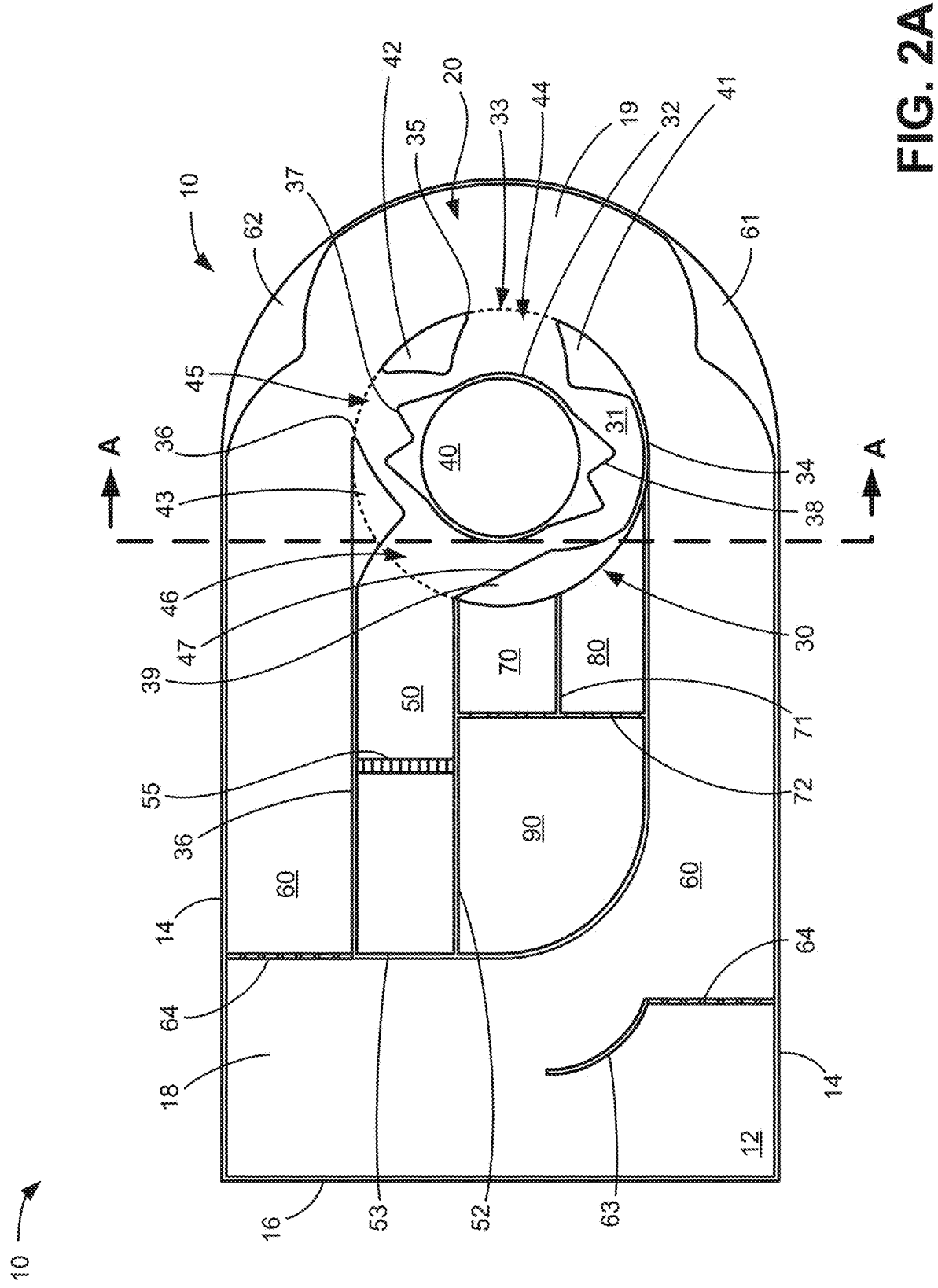
FIG. 2A is a top schematic view of the storage tray according to another implementation.
Figure 2B:
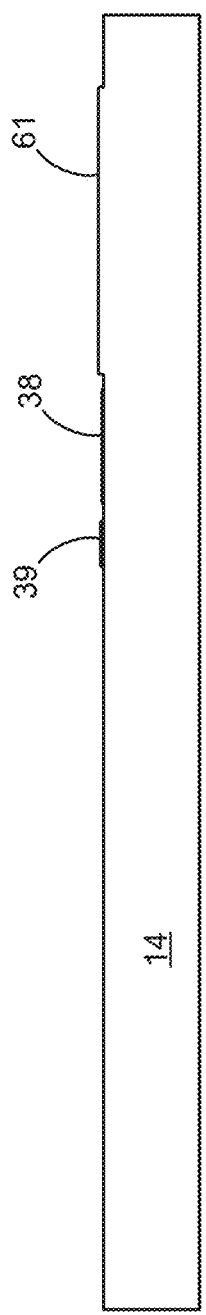
FIG. 2B is a side view of the storage tray of FIG. 2A.
Figure 2C:
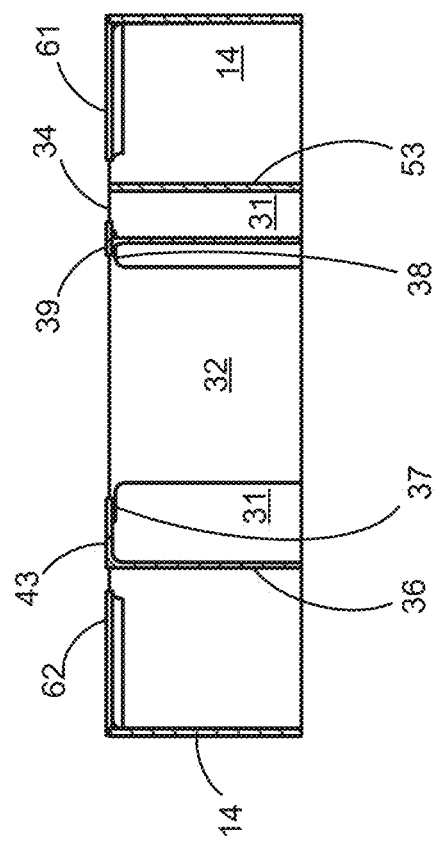
FIG. 2C is a cross-sectional end view of the storage tray of FIG. 2A.
Figure 3:
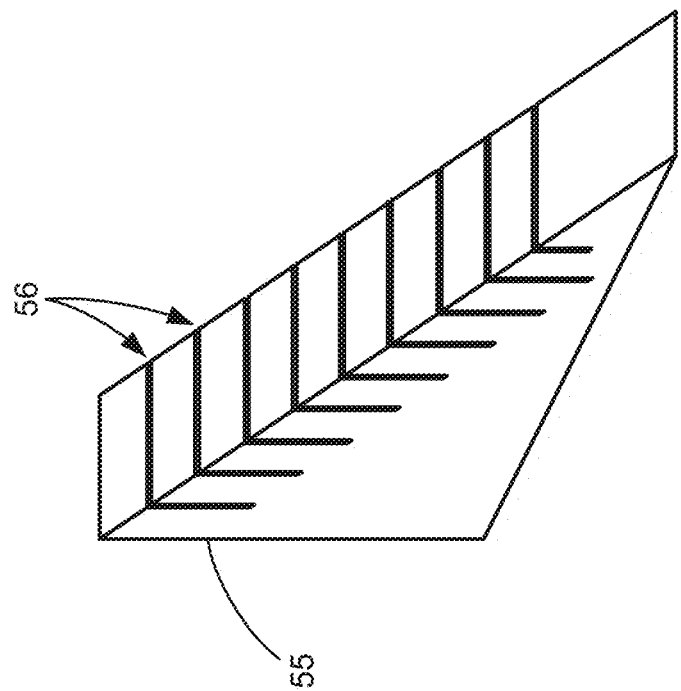
FIG. 3 is a top perspective view of the guidewire holder of FIG. 2A.

Referring collectively to FIGS. 2A-6B, a storage tray 10 includes a base 12 with a set of walls 14, 16 extending up from base 12 and around the perimeter of base 12. Base 12 may have a generally rectangular portion 18 at one end with a semicircular portion 19 at the opposite end. As shown in FIG. 2A, for example, wall 16 may extend along one end of base 12. Wall 14 may extend from an end of wall 16 at one side of base 12, around semicircular portion 19 and along the other side of base 12 to an opposite end of wall 16. Base 12 and walls 14, 16 together form an open-topped basin 20 that can hold fluid. In different implementations, corners at the intersection of base 12 and walls 14 and 16 may be square or rounded. The configuration of base 12 and walls 14 and 16 shown herein is exemplary. Other shapes for storage tray 10 may be used. For example, in another implementation, base 12 may include semicircular portions on opposite ends of base 12 (e.g., instead of having straight wall 16 on one side of base 12). In other implementations, base 12 may include reinforcing ridges, corrugation, or other features to provide additional stability. In some implementations, a removable top or lid (not shown) may be provided with storage tray 10.

Storage tray 10 may be configured in multiple sizes to suit various procedural needs. In one implementation, storage tray 10 may use a single size suitable for most procedures. According to an implementation, base 12 is about fifteen inches wide (e.g., measured along wall 16) and twenty-seven inches long (e.g., measured from wall 16 to the farthest extent of semicircular portion 19. Walls 14 and 16 may be of equal height, setting a depth of basin 20. According to an implementation, walls 14 and 16 may each be about two inches high. In other implementations, one or more of these dimensions may be greater or smaller.

As described further herein, basin 20 may be segmented into multiple sections by additional internal walls. These sections may include a wire containment section 30, a storage area 40, a wire feed section 50, a catheter channel 60, a contrast solution compartment 70, a saline solution compartment 80, and a waste/flush compartment 90. Walls (e.g., wall 14 and 16) and interior wall segments (e.g., wall segments 32, 34, 35, 36, 52, 53, 71, and 72) may extend in a generally upward direction from base 12 to form the various sections. While shown integral with basin 20 in the examples of FIGS. 1-6B, in other implementations, one or more of wire containment section 30, storage area 40, wire feed section 50, catheter channel 60, contrast solution compartment 70, saline solution compartment 80, and waste/flush compartment 90 may be provided as a removable insert onto basin 20.

Wire containment section 30 is configured to store multiple coiled guidewires in a cylindrical wire channel 31. Wire containment section 30 includes an inner wall 32 and a non-contiguous outer boundary 33 attached to base 12. Inner wall 32 may be substantially cylindrical, forming a storage area 40 for small surgical instruments as well as the inner wall for wire containment section 30. While shown as a solid section in the figures, in other implementations, inner wall 32 may include multiple non-contiguous sections, slots, etc. In one implementation, storage area 40 may be fluidly isolated from cylindrical wire channel 31. Non-contiguous outer boundary 33 for wire containment section 30 is formed from a group of wall segments including wall segment 34, wall segment 35, and a portion of wall segment 36.

Cylindrical wire channel 31 is located between the inner wall 32 and outer boundary 33. The radius of inner wall 32 is generally sized to be at least as large as a largest minimum bend radius that guidewires used in the surgical procedure can maintain without damaging the guidewires. The radius of non-contiguous outer boundary 33 is generally sized to be smaller than the maximum coil radius of an unbound guidewire, such that a coiled guidewire inserted within cylindrical wire channel 31 will exert radial force on the walls of non-contiguous outer boundary 33. In one implementation, the diameter of inner wall 32 is approximately 4.5 inches, and the outer boundary 33 diameter is approximately eight inches.

Wire containment section 30 includes inner flaps 37 and 38 extending orthogonally from the top of inner wall 32, substantially parallel to base 12. Wire containment section 30 also includes outer flaps 39, 41, 42, and 43, each extending orthogonally from the top of one of wall segments 34, 35, and 36 (and substantially parallel to base 12), as shown in FIG. 2A. Inner flaps 37, 38 and outer flaps 39, 41, 42, 43 extend over the top of cylindrical wire channel 31 to contain coiled guidewires so they do not spring out of or extend above cylindrical wire channel 31. The size and orientation of inner flaps 37, 38 and outer flaps 39, 41, 42, 43 provide openings in the top of cylindrical wire channel 31 that allow for access to, and visual inspection of, cylindrical wire channel 31. In one implementation, inner flaps 37, 38 extend horizontally from inner wall 32 to no more than half of the width of wire channel 31, and outer flaps 39, 41, 42, 43 extend horizontally from their respective wall segments 34, 35, and 36 to at least half of the width of wire channel 31.

Gaps 44 and 45 between wall segments 34, 35, and 36 provide openings to cylindrical wire channel 31 large enough for a hand to comfortably fit, so that coiled guidewires may be loaded into the channel with ample clearance. Gaps 44 and 45 also allow the user to grab any wire ends that may have erroneously been pulled from wire feed section 50 into cylindrical wire channel 31. In one implementation, gaps 44 and 45 may have the same or different dimensions. In one example, gap 44 may be at least one inch wide and gap 45 may be at least two inches wide (e.g., measured along a circumference of non-contiguous outer boundary 33). A gap 46 between wall segments 34 and 36 serves as an entrance for guidewires from wire containment section 30 to wire feed section 50. While embodiments described herein show three gaps 44, 45, and 46, in other implementations fewer (e.g., one or two) or more (e.g., four or five) gaps may be included around non-contiguous outer boundary 33. In still another implementation, a ridge or short wall section (e.g., less than 2 centimeters high) may be used in one or more of gaps 44, 45, and 46. In another example, a continuous wall may be included from gap 46 around boundary 33 of wire containment section 30 to fluidly isolate cylindrical wire channel 31 from catheter channel 60.

In one implementation, outer flap 39 may visually guide a user to start loading the wire from the adjacent opening. More particularly, the shape of outer flap 39 may include a straight edge 47 forming an elongated opening adjacent to gap 46. As described further herein, the opening along straight edge 47 may provide a convenient entry point for loading coiled wires into cylindrical wire channel 31.

Figure 4:
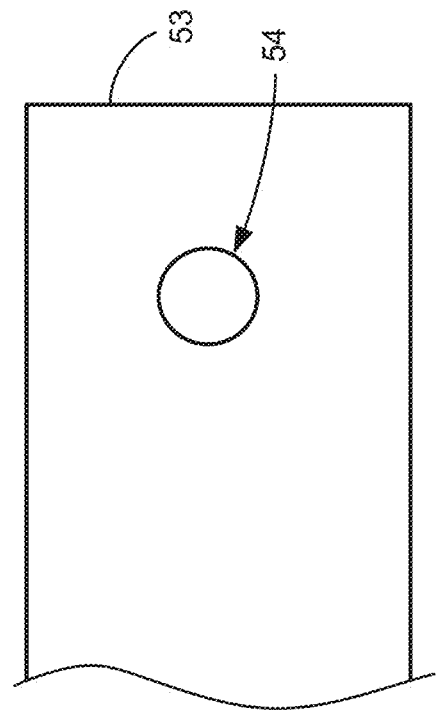
FIG. 4 is an end view of a portion of a wall segment for the wire feed section of FIG. 2A.

Wire feed section 50 is configured to hold one end of each of the guidewires stored in wire containment section 30. As shown, for example, in FIG. 2A, wire feed section 50 may be formed from wall segments 36, 52, and 53. In one implementation, wall segments 36 and 52 may be solid segments. Wall segment 53 extends from an end of wall segment 36 beyond an end of wall segment 52, bends as shown in FIG. 2A, and joins wall segment 34. FIG. 4 provides a side view of the portion of wall segment 53 between wall segments 36 and 52. As shown, for example, in FIG. 4, wall segment 53 may include one or more apertures 54, between the ends of wall segments 36 and 52, for introducing a guidewire from wire feed section 50 to an entrance point (e.g., on a patient). Aperture 54 may generally be sized with a large enough diameter to receive any of guidewires stored within cylindrical wire channel 31. When a guidewire end is threaded through aperture 54, the location of aperture 54 in wall segment 53 ensures that a direction of a pull on the guidewire, as it exits cylindrical wire channel 31, is substantially parallel to base 12.

Wire feed section 50 also includes a guidewire holder 55. As shown, for example, in FIG. 3, guidewire holder 55 may generally be right-triangular shaped with multiple slots 56 opening along the hypotenuse of the triangular-shaped element to hold individual wires. Guidewire holder 55 may be formed from plastic, foam, or another malleable material and secured (e.g., to base 12) between wall segments 36 and 52. In another implementation, guidewire holder 55 may be formed from a rigid material with slots configured to constrain guidewires therein. Guidewires may be inserted into slots 56 and secured by frictional contact to prevent recoil of the guidewires into wire containment section 30. The slope of guidewire holder 55 allows slots 56 to be placed at different heights, relative to base 12, allowing for easier visual and tactile distinction between wires installed in guidewire holder 55. Thus, ends of the guidewires may be separated in wire feed section 50 for easy identification, selection, and removal from wire containment section 30. The number of slots 56 in guidewire holder 55 may correspond to the number of guidewires to be stored in cylindrical wire channel 31. In one implementation, guidewire holder 55 may include at least six slots with openings at different distances from the base. In other implementation, more or few slots 56 may be included in guidewire holder 55.

Catheter channel 60 may generally surround wire containment section 30, wire feed section 50, contrast solution compartment 70, saline solution compartment 80, and waste/flush compartment 90. The outer boundary of catheter channel 60 includes walls 14 and 16. The inner boundary of catheter channel 60 is generally defined by wall segments 34, 35, 36, and 53 described above. Catheter channel 60 may store catheters, balloons, and other instruments. In one implementation, as shown in FIG. 2A, catheter channel 60 is in fluid communication with wire containment section 30 and wire feed section 50.

Catheter channel 60 includes flaps 61 and 62, each extending orthogonally from the top of wall 14 (and substantially parallel to base 12), as shown in FIG. 2A. Flaps 61 and 62 extend over the top of a portion of catheter channel 60 to contain catheters, tubing, and the like, from springing out of or extending from catheter channel 60 and becoming exposed to contamination. In other implementations, additional flaps (not shown) extending over the top of other portions of catheter channel 60 may also be included. Catheter channel 60 may also include one or more dividers 63 to separate objects coiled in catheter channel 60. Divider 63 may be configured similar to a wall segment, such as the bend portion of wall segment 53, and may act as an additional structural support for storage tray 10.

Catheter channel 60 may further include one or more catheter/instrument holders 64. As shown, for example, in FIG. 5, each of catheter/instrument holders 64 may include a wall segment with various sized openings 65 or slots, extending from the top of the wall segment, to hold and/or separate tubing for catheters. In one implementation, openings 65 may be "J"-shaped openings to securely hold tubing, especially for the hooked ends of pig-tailed catheters. In other implementations, some openings 65 may be of different shapes (e.g., "V"-shaped) and sizes with some openings 65 large enough to accommodate multiple tubes simultaneously.

Contrast solution compartment 70 may store a fluid in isolation from other sections of basin 20. The boundaries of contrast solution compartment 70 include wall segment 71 and portions of wall segments 34, 52 and 72. In one implementation, contrast solution compartment 70 may store diagnostic contrast agents or other fluids used during surgical procedures. Wall segment 72 may also include one or more notches 73 in which syringes or other devices may rest. In one implementation, notches 73 (shown in FIGS. 6A and 6B) may have various sizes to accommodate different types of devices. Markings or indicia, such as volumetric gauge markings 74 (e.g., shown in milliliters), may be included on a surface of one or more of wall segments 34, 52, 71, and 72 that face the interior of contrast solution compartment 70, as shown in FIG. 6A on a front side of wall segment 72.

Saline solution compartment 80 may also store fluids in isolation from other sections of basin 20. The boundaries of saline solution compartment 80 include wall segment 72 and portions of wall segments 52 and 53. In one implementation, saline solution compartment 80 may store saline solution. Markings or indicia 82, such as volumetric gauge markings (e.g., shown in milliliters), may be included on a surface of one or more of wall segments 52, 53, or 72 that face the interior of saline solution compartment 80, as shown in FIG. 6B on a back side of wall segment 72.

Waste/flush compartment 90 may store fluids in isolation from other sections of basin 20. The boundaries of waste/flush compartment 90 include wall segment 71 and portions of wall segments 34, 53, and 72. In one implementation, waste/flush compartment 90 may store discarded fluids from a surgical procedure.

The arrangement of wire containment section 30, storage area 40, wire feed section 50, catheter channel 60, contrast solution compartment 70, saline solution compartment 80, and waste/flush compartment 90 inside storage tray 10, as shown in the example of FIG. 2A, is exemplary. In other embodiments, sections may be arranged differently within storage tray 10. For example, the orientation of wire containment section 30, storage area 40, wire feed section 50, contrast solution compartment 70, saline solution compartment 80, and waste/flush compartment 90 may be flipped to provide more favorable guidewire storage and extraction for left-handed users. In other embodiments, fewer or more sections may be included in storage tray 10. For example, two wire feed sections 50 (e.g., a right-hand side and a left-hand side) may be included extending from different gaps in non-contiguous outer boundary 33 of storage tray 10, while one or more of contrast solution compartment 70, saline solution compartment 80, and waste/flush compartment 90 may be re-sized or eliminated.

Storage tray 10 generally may be made from a relatively light, rigid, and smooth material that is water resistant, such as plastic. For example, in one implementation, storage tray may include a combination of injected molded polypropylene and thermoformed plastic. In another implementation, storage tray 10 may be formed using ABS (Acrylonitrile Butadiene Styrene) with three-dimensional (3D) printing. In still another implementation, storage tray 10 may be molded in one or more sections and assembled. According to one implementation, the base (e.g., base 12), walls (e.g., wall 14 and 16), and interior wall segments (e.g., wall segments 32, 34, 35, 36, 52, 53, 71, and 72) may be of the same material and thickness. The flaps (e.g., flaps 37, 38, 39, 41, 42, 43, 61, and 62) may be made of the same material as the walls, but some flaps may be thinner than the wall segments so as to flex when receiving coiled guidewires or tubes. In one implementation, wire holder 55 and/or catheter/instrument holders 64 may be attached after other parts of storage tray 10 are formed. In another implementation, storage tray 10 may be formed from a combination of materials. For example, some or all of storage tray 10 may be formed from a collapsible waterproof fabric (such as polyester) supported with rigid ribs (e.g., ABS or polyethylene). In still other implementations, storage tray 10 may be formed from stainless steel, aluminum, or other materials that may be sterilized for reuse.

In still other implementations, one or more portions of storage tray 10 may be formed using double walls to form base 12 and some or all of wall segments 32, 34, 35, 36, 52, 53, 71, and 72 as a single continuous piece. Double wall construction may enable, for example, nested packing of components for storage trays 10.

Portions of storage tray 10 are filled with storage liquid, which submerges (or partially submerges) the wires and catheters while not in use and provides lubrication during removal of the guidewires from storage tray 10, as described further below.

FIGS. 7A-7E provide simplified schematics for using storage tray 10, according to an implementation. To use storage tray 10 during a surgical procedure, storage liquid (e.g., heparinized saline or another sterile solution) may be added to wire containment section 30, wire feed section 50, and/or catheter channel 60. Heparinized saline provides anti-coagulative coating that is generally required before an item (such as wire or catheter) is introduced or re-introduced into a patient. The storage liquid (not shown) may serve to (1) moisten stored devices, such as guidewires 100 and catheters, (2) weigh down storage tray 10 and stabilize it on a surface, (such as a surgical end table, and (3) lubricate wall surfaces, particularly the outside of inner wall 32. In one implementation, wire containment section 30, wire feed section 50, and catheter channel 60 is filled with liquid to a depth that submerges the wires and catheters while not in use (e.g., 0.5 to 1 inch deep).

Figure 7A:
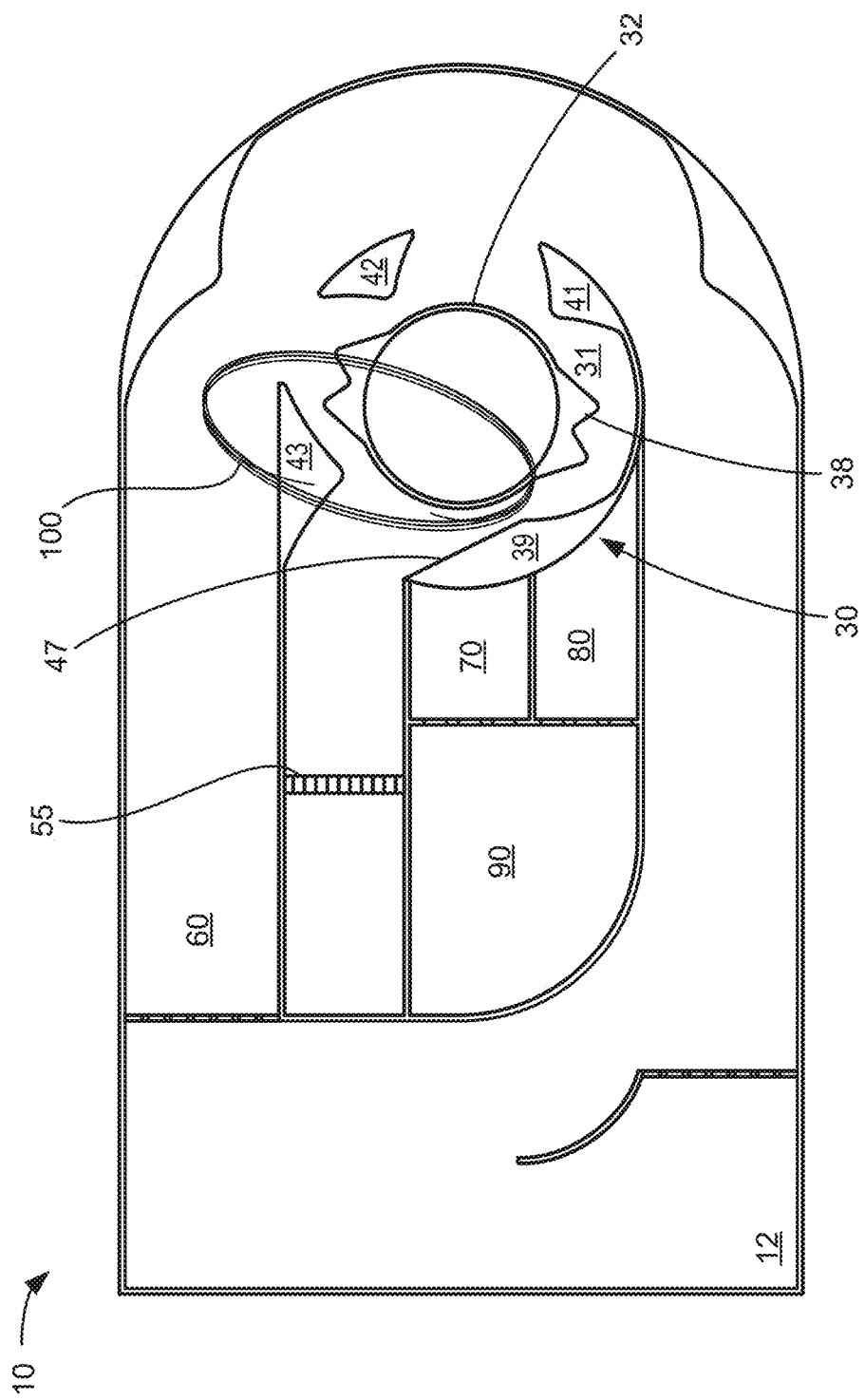
FIGS. 7A-7E are simplified schematics of a process for using the storage tray of FIG. 1, according to an implementation described herein.
Figure 7B:
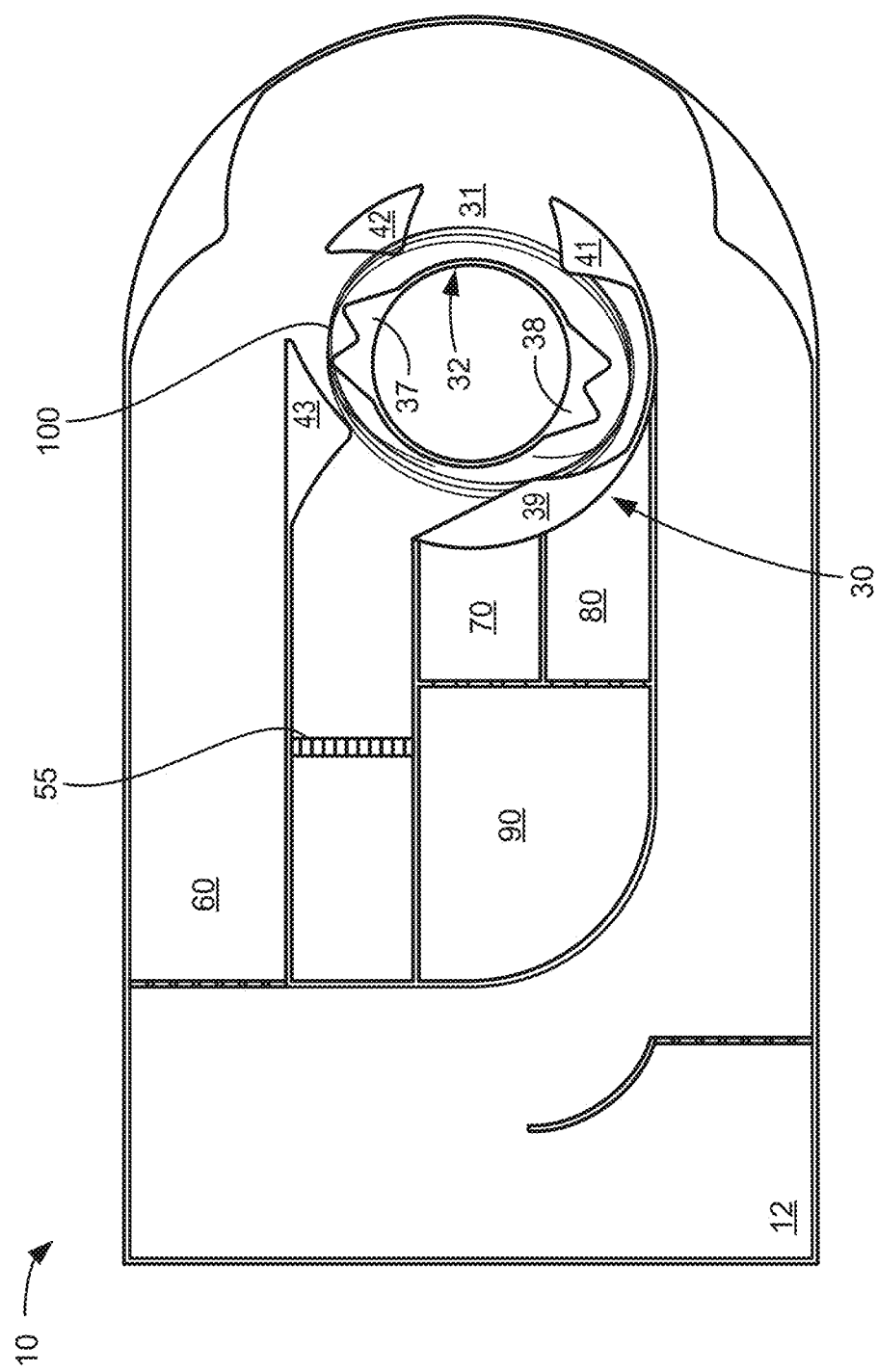

One or more guidewires 100 are loaded into cylindrical wire channel 31 by coiling the wires (e.g., by hand) into an approximate 5-to-8 inch diameter coil. A 5-to-8 inch diameter coil is the coil size that surgery technicians are typically trained to coil and store wires during procedures. The coiled wires 100 are pushed down under inner flaps 37, 38 and outer flaps 39, 41, 42, and 43. In one implementation, as shown in FIG. 7A, a portion of coil 100 is first inserted between outer flap 39 and inner wall 32, along edge 47. Coil 100 is then pressed down next to inner flap 38 and under outer flap 41, as shown in FIG. 7B. Coil 100 is then pressed under outer flap 42, next to inner flap 37, and under outer flap 43 to completely insert the coil into cylindrical wire channel 31, as shown in FIG. 7C.

Figure 7C:
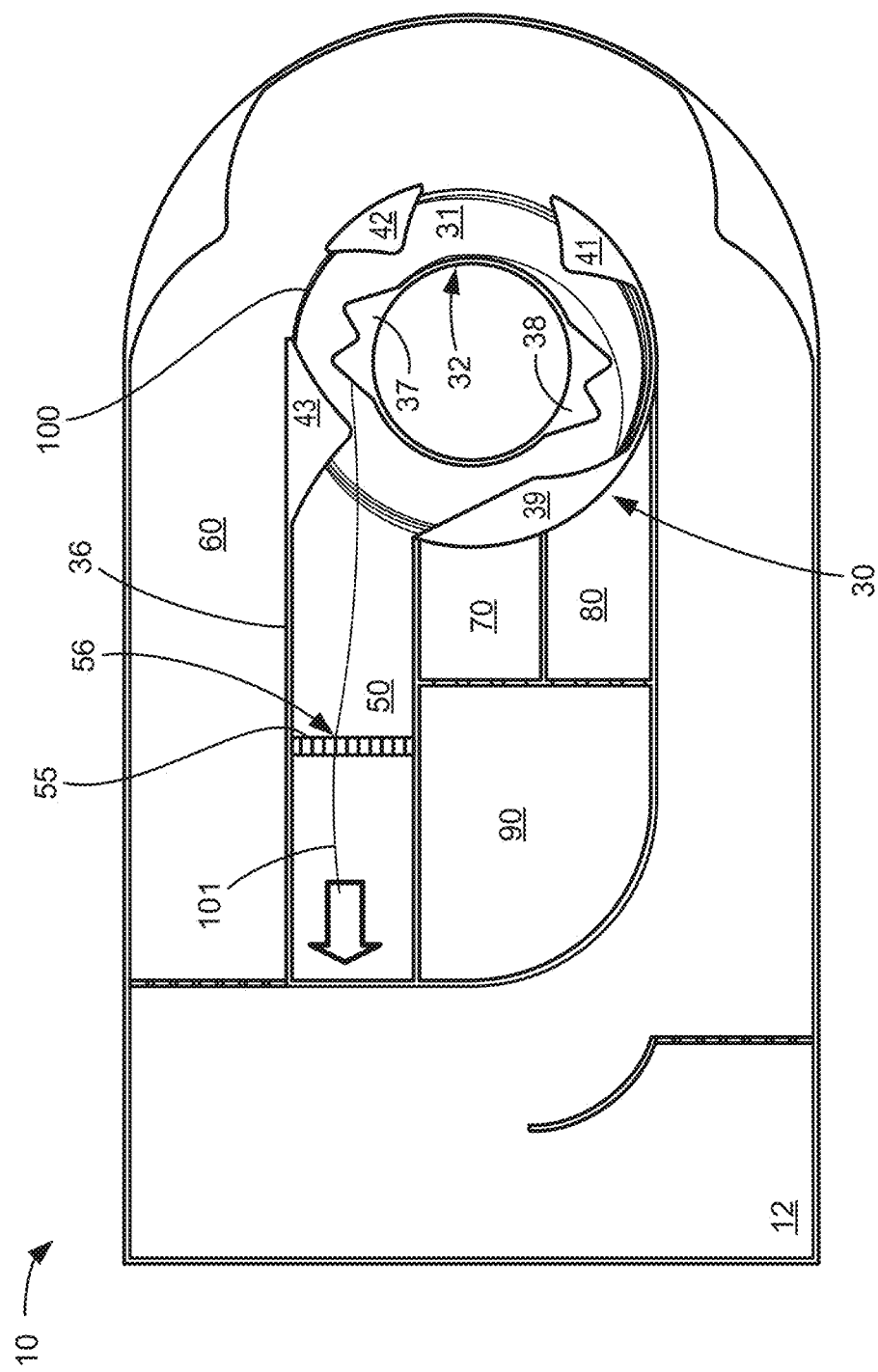

After insertion into cylindrical wire channel 31, the technician releases the coil 100, while holding onto a flexible distal end 101, and placing the end 101 into one of slots 56 in wire holder 55, as further shown in FIG. 7C. In one implementation, the orientation of inserted wire coil 100 will extend from inner wall 32 counterclockwise to holder 55. When released, resiliency of the guidewire material causes the coil 100 to expand until it rests along the non-contiguous outer boundary 33 for wire containment section 30 (i.e., formed of wall segments 34, 35, and 36). Outer flaps 39, 41, 42, and 43 retain the coiled wire vertically within cylindrical wire channel 31, preventing the wire from springing out and potentially becoming contaminated. Wire holder 55 keeps the end 101 of the guidewire from being retracted into cylindrical wire channel 31. Additional coiled guidewires (not shown) may be inserted in the same manner, with the respective ends being place in different slots 56 of wire holder 55. In another implementation, multiple coils of guidewires may be inserted into cylindrical wire channel 31 simultaneously. The different slot 56 placement visually separates the wires so the technician can quickly identify and select a particular wire to be used during a procedure. In one implementation, up to 6, 8, 12, or more coiled guidewires may be stored in wire containment section 30.

Figure 7D:
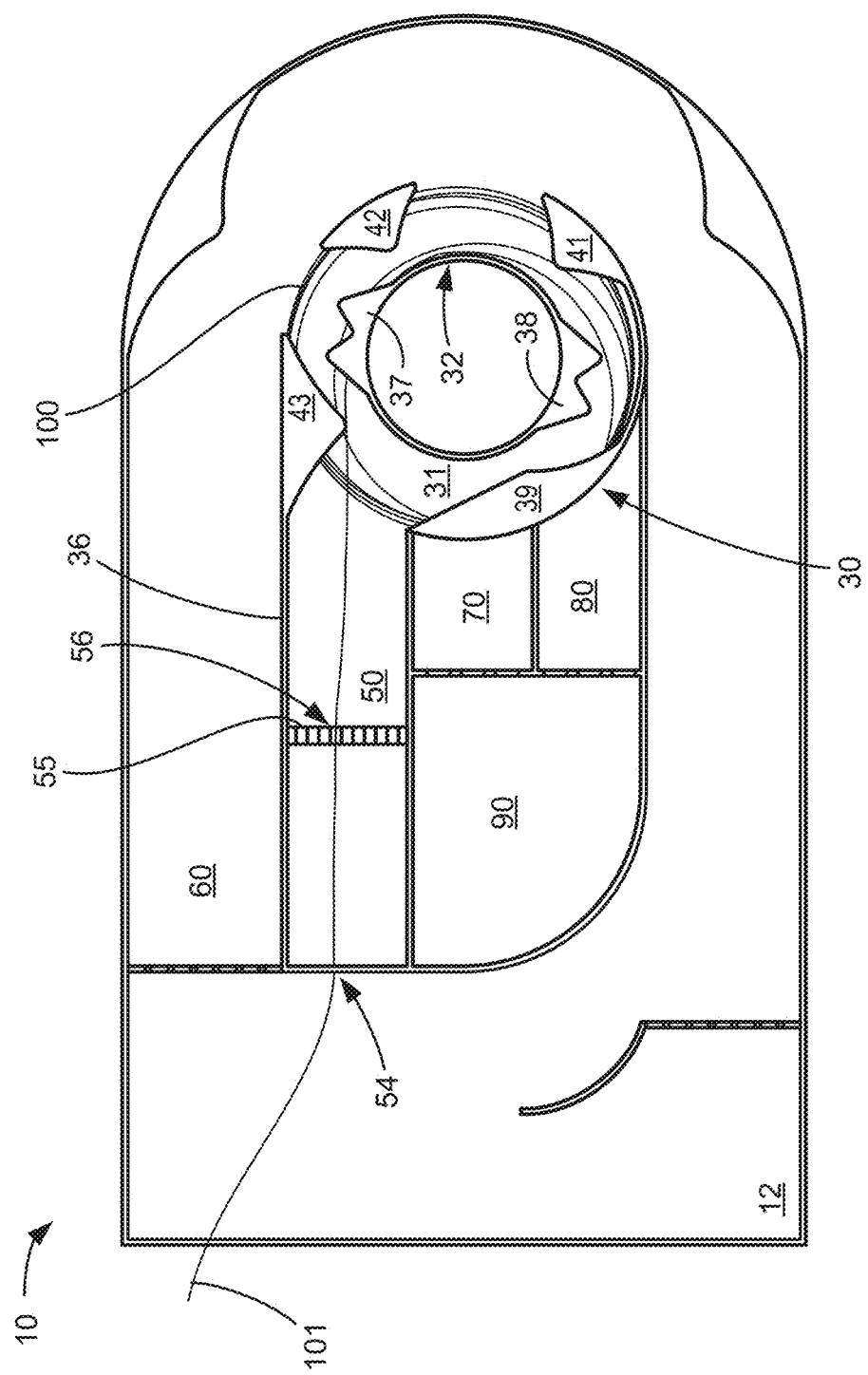

Referring to FIGS. 7C and 7D, inner wall 32 provides a rigid wall for a wire 100 in use to separate wire 100 from the other wires in cylindrical wire channel 31. Pulling the end of one wire (e.g., end 101 of the wire "in use") in the direction of the arrow shown in FIG. 7C, causes a portion of the wire 100 to be pulled against the inner wall 32, separating it from the other wires (which will tend to expand against the outer circular wall segments for wire containment section 30), so other wires do not become tangled with the wire in use. In some instances, lubrication on wire 100 and/or the storage liquid in cylindrical wire channel 31 may allow for wire 100 to slide more easily against inner wall 32.

Referring to FIG. 7D, when guidewire 100 is selected for use in a surgical procedure, end portion 101 of guidewire 100 is removed from slot 56 and pulled horizontally from cylindrical wire channel 31 through wire feed section 50. Inner flaps 37 and 38 prevent wire 100 from slipping up and over inner wall 32 when guidewire 100 is pulled along inner wall 32. In one implementation, end portion 101 of guidewire 100 may be inserted through aperture 54 of wall segment 53. Use of aperture 54 may allow one-handed removal of guidewire 100 while maintaining a correct orientation of pull from inner wall 32. Thus, aperture 54 ensures that tension (i.e., the direction of pull) on guidewire 100 as it exits cylindrical wire channel 31 remains substantially parallel to both base 12 and wall segment 36.

Figure 7E:
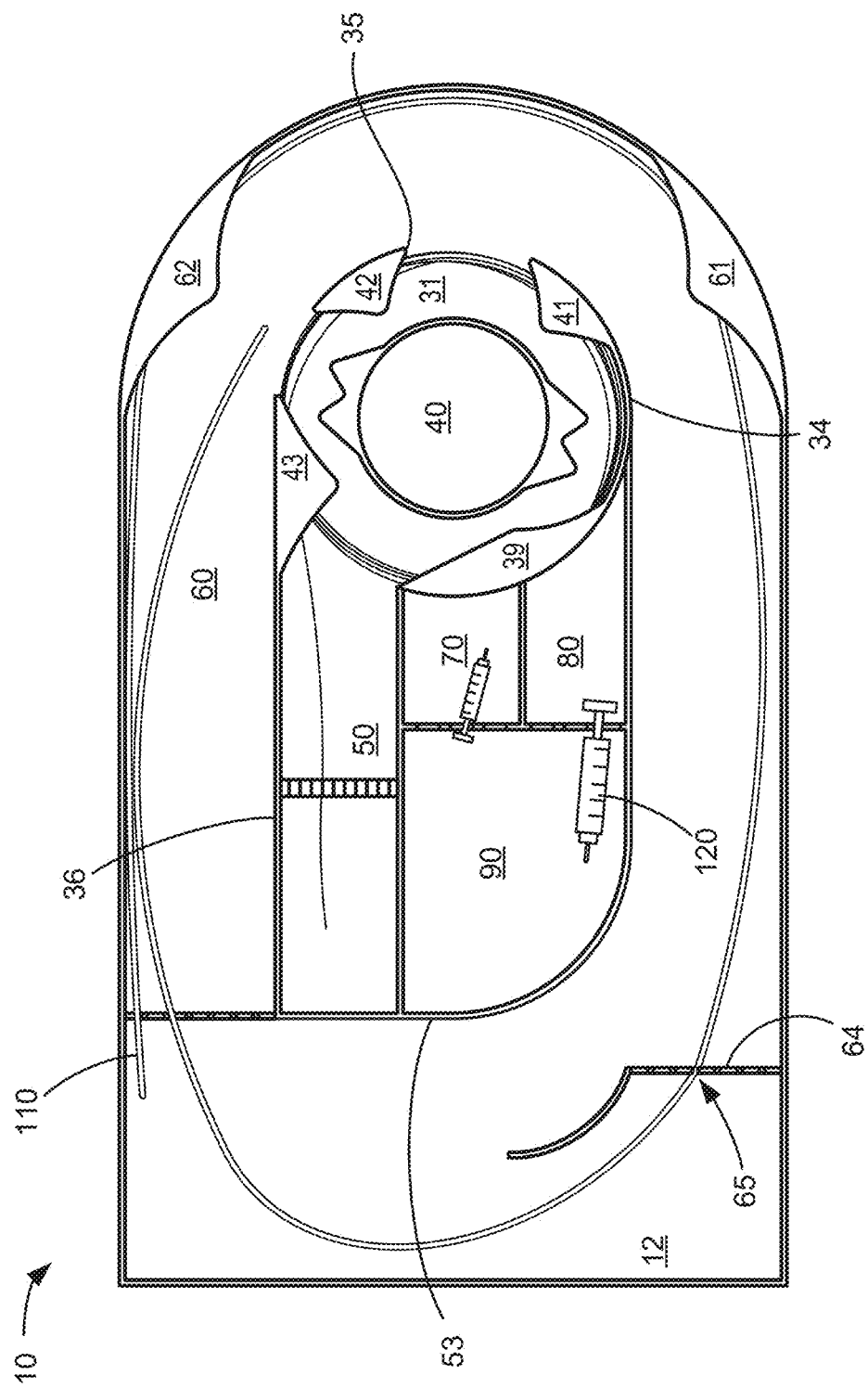

Referring to FIG. 7E, catheter channel 60 of storage tray 10 holds catheters, tubes (e.g., tube 110) and other instruments. Catheter channel 60 wraps around the other sections of storage tray 10 (e.g., wire containment section 30, storage area 40, wire feed section 50, contrast solution compartment 70, saline solution compartment 80, and waste/flush compartment 90), so that catheters and other instruments can be stored neatly while not in use and visually identified when needed. In one implementation, catheter channel 60 is approximately 3 inches across (e.g., the width between wall 14 and wall segment 36) to accommodate up to ten catheters or instruments, of 60 inches (about 152) cm in length or longer.

One or more tubes 110 are loaded into catheter channel 60 by looping tube (e.g., by hand) around interior wall segments 34, 35, 36, and 53. The tube 110 may be pushed down under flaps 61 and 62. In one implementation, as shown in FIG. 7E, a portion of tube 110 is inserted into an opening 65 of catheter/instrument holder 64 to further secure tube 110. Other instruments may be stored in respective sections (e.g., storage area 40, contrast solution compartment 70, saline solution compartment 80, and waste/flush compartment 90). For example, as shown in FIG. 7E, a syringe 120 for saline solution may be stored in waste/flush compartment 90, resting in one of notches 73. Another syringe may be stored in contrast solution compartment 70, as shown.

Figure 8:
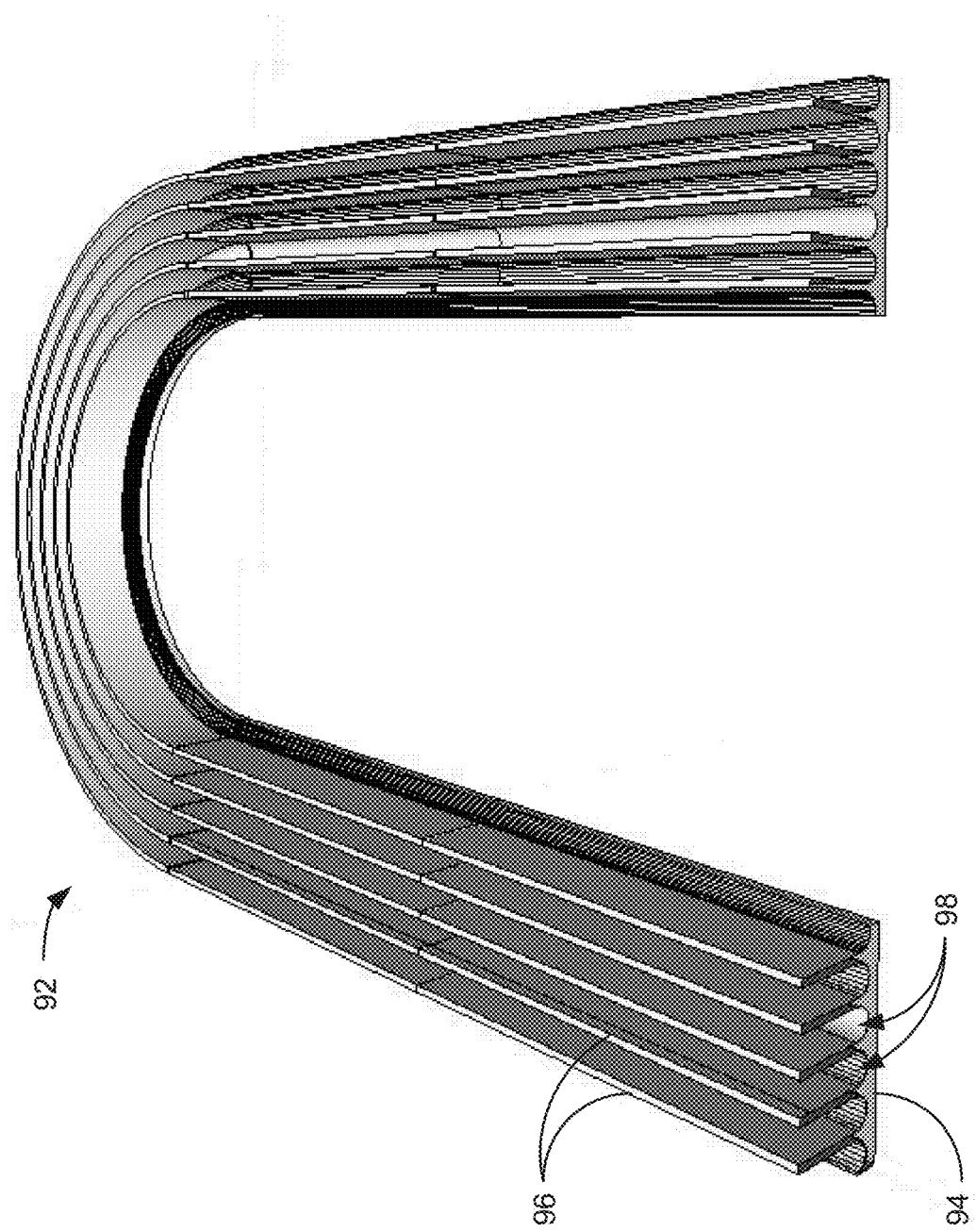
FIG. 8 is a top perspective view of a catheter channel insert.
Figure 9:
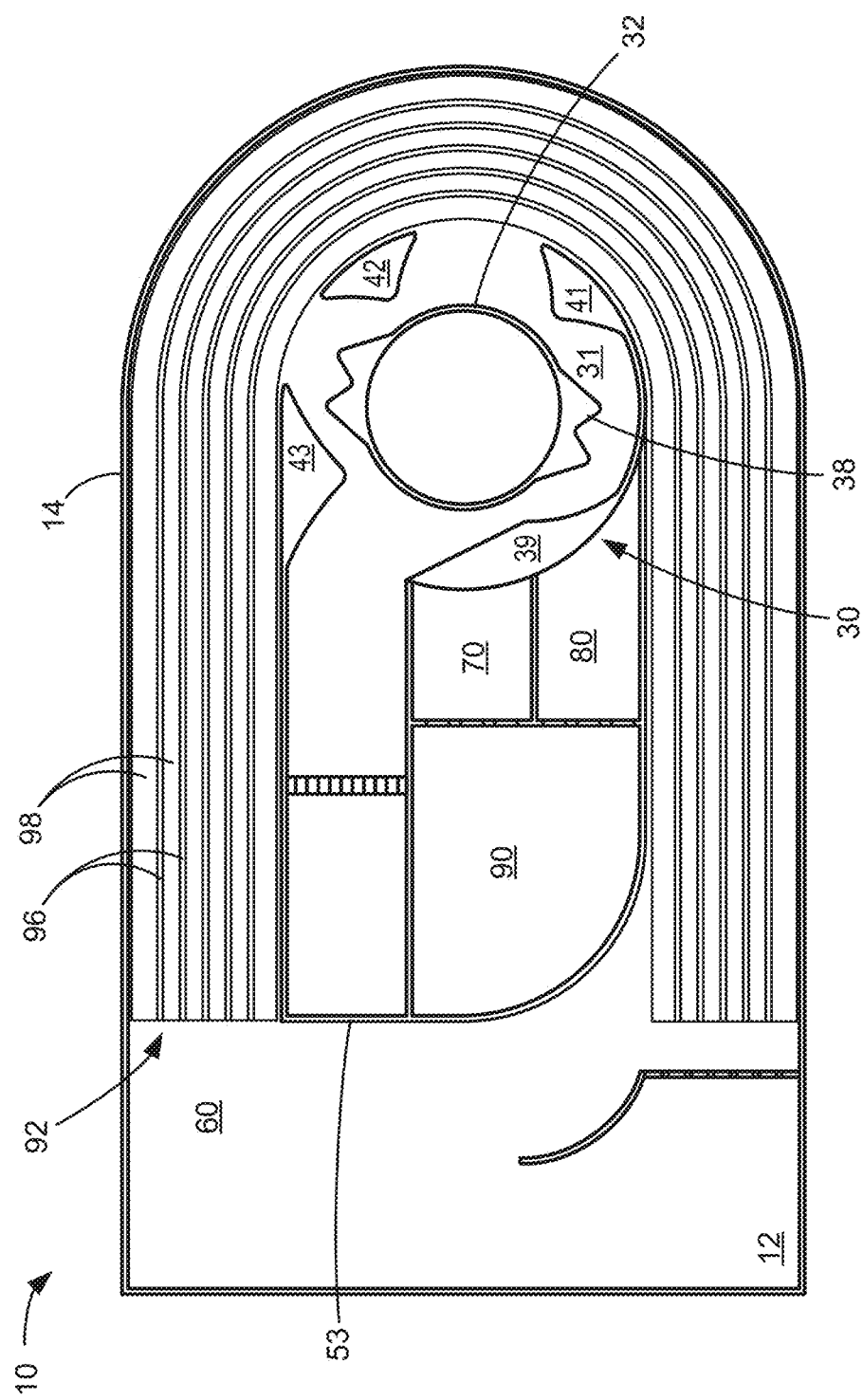
FIG. 9 is a is a top schematic view of the storage tray of FIG. 1 with the catheter channel insert.

FIG. 8 is a top perspective view of a catheter channel insert 92, according to an implementation. FIG. 9 is a is a top schematic view of a storage tray with the catheter channel insert 92 installed. According to one implementation, catheter channel insert 92 may be a modular/removable component for insertion into a portion of catheter channel 60. Catheter channel insert 92 may include a base portion 94 sized to rest on base 12 in catheter channel 60. In one implementation, catheter channel insert 92 may be secured to base 12 by adhesives, friction, or interference fit. Multiple dividing walls 96 extend upwardly from base 12 and run generally parallel to wall 14 when installed along a portion of channel 60. Dividing walls 96 may form multiple paths 98 into which catheters, balloons, and the like may be inserted and separated. Five dividing walls 96, forming 6 paths 98, are shown in FIGS. 8 and 9. In other implementations, as few as two or ten or more paths 98 may be included in catheter channel insert 92. In another implementation, the width/spacing of dividing walls 96 may be varied to form paths 96 of different widths (e.g., that can hold different sized catheters or other instruments).

As shown in FIG. 9, use of catheter channel insert 92 may preclude the need for flaps 60 and 61 over catheter channel 60. Thus, flaps 60 and 61 are not included in storage tray 10 in the configuration of FIG. 9.

Figure 10:
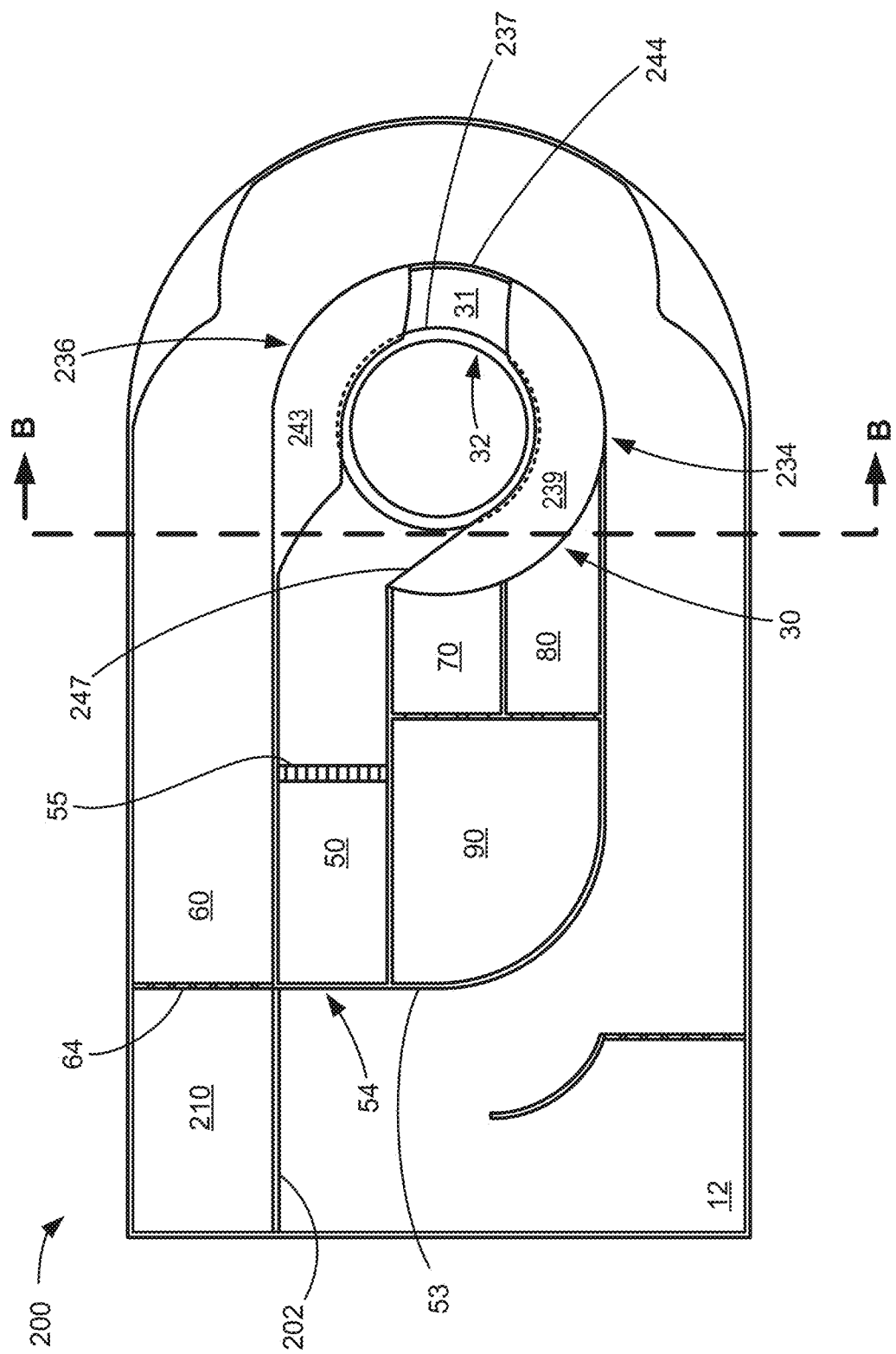
FIG. 10 is a top schematic view of a storage tray according to another implementation.
Figure 11:
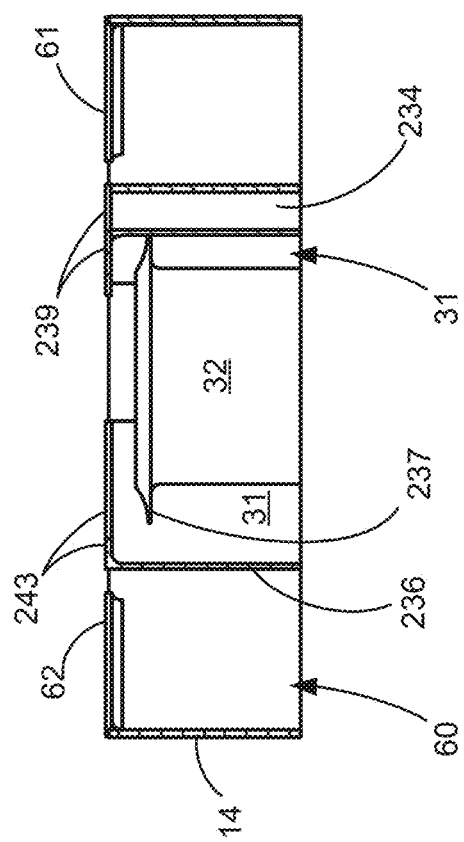
FIG. 11 is a cross-sectional end view of the storage tray of FIG. 10.

FIG. 10 a top schematic view of a storage tray 200 according to another implementation described herein. FIG. 11 is a cross-sectional view of storage tray 10 along line B-B of FIG. 10. As described below, storage tray 200 includes a different configuration of flaps and wall segments in wire containment section 30 and a saline storage area 210. Otherwise, storage tray 200 may include features of storage tray 10 described above.

Referring collectively to FIGS. 10 and 11, wire containment section 30 is configured to store multiple coiled guidewires in cylindrical wire channel 31. Wire containment section 30 includes a inner wall 32 attached to base 12 and an outer boundary 33. Outer boundary 33 is formed from wall segments including wall segment 234 and a portion of wall segment 236. Cylindrical wire channel 31 is located between the inner wall 32 and outer boundary 33.

Wire containment section 30 includes an inner flap 237 extending substantially orthogonally from inner wall 32 over cylindrical wire channel 31. Wire containment section 30 also includes outer flaps 239 and 243, each extending orthogonally from one of wall segments 234 and 236 as shown in FIG. 2A. Flaps 237, 239, and 243 extend over cylindrical wire channel 31 to contain coiled guidewires so they do not spring out of or extend above cylindrical wire channel 31.

According to an implementation, the height of inner wall 32 may be different than the height of wall segments 234 and 236. Additionally, or alternatively, flaps 237 and may be at a different height (e.g., distance above base 12) than flaps 239 and 243.

The size and orientation of flaps 237, 239, and 243 provide an opening in the top of cylindrical wire channel 31 that allow for insertion of coiled wires into cylindrical wire channel 31. In one implementation, inner flap 237 extends horizontally from inner wall 32 at a lower height than outer flaps 239 and 243 extend horizontally from their respective wall segments 234 and 236. Thus, in some implementations, inner flap 237 and outer flaps 239 and 243 may overlap above cylindrical wire channel 31. In other implementations, inner flap 237 and outer flaps 239 and 243 may not overlap and/or may extend horizontally to different widths over cylindrical wire channel 31 (extending away from wall 32 and wall segments 234 and 236, respectively).

According to another implementation, as shown in FIG. 10, an additional wall segment 244 may be included between wall segments 234 and 236. Wall segment 244 may be shorter (e.g., distance above base 12) than wall segments 234 and 236 and may not include a flap extending over cylindrical wire channel 31. In one implementation, wall segment 244 may be about one inch (e.g., 2.5 cm) in height. Wall segment 244 may be contiguous with wall segments 234 and 236 to prevent fluid communication between cylindrical wire channel 31 and catheter channel 60. Thus, in the configuration shown in FIG. 10, wire containment section 30 and wire feed section 50 are in fluid isolation from catheter channel 60 (e.g., assuming the fluid levels in wire containment section 30, wire feed section 50, and catheter channel 60 do not exceed the height of wall segment 244 or the bottom of aperture 54). Because wall segment 244 is shorter than the adjacent wall segments and does not include a flap, As further shown in FIG. 10, storage tray 200 may also include a saline reservoir 210. Saline reservoir 210 may include a shallow compartment that stores fluid in isolation from other sections of storage tray 200. In one implementation, saline reservoir 210 may be bounded by a short wall 202, the bottom (i.e., non-slotted) portion of catheter/instrument holders 64, and portions of wall 14 and wall 16. In another implementation, saline reservoir 210 may be formed as a recess below the level of base 12. Saline reservoir 210 may be used, for example, to hold a smaller amount of fluid than would be required to cover catheter channel 60. Thus, at the preference of a surgeon, a catheter or instrument could be stored in a relatively dry catheter channel 60 and drawn through saline reservoir 210 to moisten the catheter or instrument when removing it from catheter channel 60.

While storage tray 10 and storage tray 200 include some different features, in other implementation, features of storage tray 10 and storage tray 200 may be combined or substituted. For example, saline reservoir 210 may be included in storage tray 10. As another example, catheter channel insert 92 may be included in storage tray 200. In still another example, the height differences of flaps described in storage tray 200 may be applied to flaps in storage tray 10.

Figure 12:
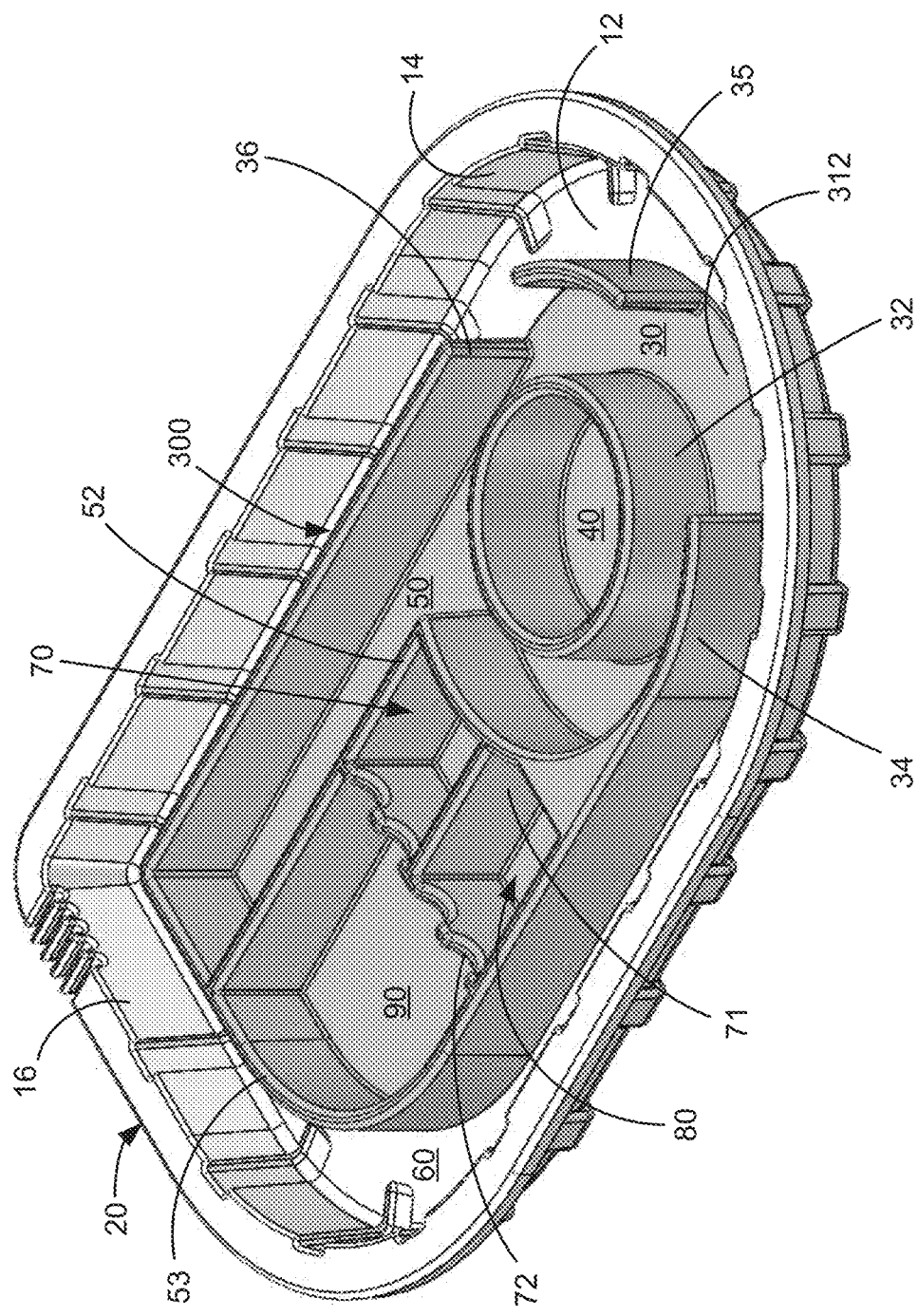
FIG. 12 is a perspective view of a portion of the storage tray, according to another implementation.

In another implementation, storage tray 10 and/or storage tray 200 may be assembled with modular components. Thus, wire containment section 30, storage area 40, wire feed section 50, catheter channel 60, contrast solution compartment 70, saline solution compartment 80, waste/flush compartment 90, and/or saline reservoir 210, for example, may be made from separate wall segments and/or with separate base pieces which may be arranged differently than shown above. These modular components may, for example, be snapped into place or removed on location to accommodate particular procedural needs or preferences. For example, as shown in FIG. 12, basin 20 (e.g., base 12 and wall 14 and 16) may be formed as a separate basin and the interior wall segments (e.g., wall segments 32, 34, 35, 36, 52, 53, 71, and 72 forming wire containment section 30, storage area 40, wire feed section 50, catheter channel 60, contrast solution compartment 70, saline solution compartment 80, and waste/flush compartment 90) may be formed as a separate unit 300 that attaches to or sits upon basin 20. In one implementation, unit 300 may include a base 312 to support the wall segments of unit 300. Flaps (e.g., flaps 37, 38, 39, 41, 42, 43, 61, and 62 or flaps 237, 239, and 243) are not shown in FIG. 12 for clarity.

According to implementations described herein, a storage tray provides storage for multiple types of wires, catheters, and other instruments used during surgical procedures. Designated wire and catheter channels are filled with saline or other solutions to receive objects and keep them moist. Multiple coiled wires may be stored in a common wire channel, and multiple catheters/tubes may be stored in a differed common catheter channel, thus conserving storage/table space and simplifying surgical preparations. While the coiled wires are stored together in a single channel, ends of the coiled objects may be stored in separate slots for easy selection and removal. Flaps over the designated wire and catheter channels allow coiled objects to be stored in liquid solutions without springing apart or extending over the sides/ends of their compartments. In one implementation, a selected guidewire may be removed from the storage tray by pulling the end horizontally away from the channel.

As set forth in this description and illustrated by the drawings, reference is made to "an exemplary embodiment," "an embodiment," "embodiments," etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment (s). The same applies to the term "implementation," "implementations," etc.

The foregoing description of embodiments provides illustration, but is not intended to be exhaustive or to limit the embodiments to the precise form disclosed. Accordingly, modifications to the embodiments described herein may be possible. For example, various modifications and changes may be made thereto, and additional embodiments may be implemented, without departing from the broader scope of the invention as set forth in the claims that follow. The description and drawings are accordingly to be regarded as illustrative rather than restrictive.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items. The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction used in the description of the present application should be construed as critical or essential to the invention unless explicitly described as such.

What is claimed is:

1. A device for use in a surgical procedure, comprising:
    a base and a set of walls forming a basin that holds a liquid;
    a wire containment section within the basin including:
        a wire channel,
        an inner wall extending up from the base forming an inner boundary of the wire channel,
        at least one first flap extending orthogonally from the inner wall and over first portions of the wire channel,
        one or more wall segments extending up from the base forming an outer boundary of the wire channel, and
        at least one second flap extending orthogonally from the one or more wall segments and over second portions of the wire channel; and
    a wire feed section within the basin and in fluid communication with the wire channel, the wire feed section including a wire holder with multiple slots, each of the multiple slots being configured to hold an end portion of a wire,
    wherein the wire containment section is configured to receive multiple coiled guidewires inserted below the at least one first and second flaps into the wire channel so that the coiled guidewires expand against the one or more wall segments, and
    wherein pulling one end portion of one of the multiple coiled guidewires through the wire feed section causes the one of the multiple coiled guidewires to slide along the inner wall for separation and removal.

2. The device of claim 1, wherein at least one of the first flap and the second flap extends horizontally over least half of the width of the wire channel.

3. The device of claim 1, the wire feed section further comprising:
    an interior wall segment extending up from the base, the interior wall segment including an aperture sized to receive a largest of the multiple coiled guidewires.

4. The device of claim 1, further comprising:
    a storage area within the inner wall, wherein the storage area is fluidly isolated from the wire channel.

5. The device of claim 1, further comprising:
    a catheter channel surrounding the wire containment section and the wire feed section, the catheter channel including a third flap extending orthogonally from the set of walls and above the catheter channel.

6. The device of claim 5, further comprising:
at least one internal wall segment within the catheter channel, the at least one internal wall segment having various sized openings to hold tubing and catheters associated with the surgical procedure.

7. The device of claim 1, wherein the wire holder includes a malleable material secured to an internal wall of the wire feed section.

8. The device of claim 7, wherein the wire holder includes at least six slots with openings at different distances from the base.

9. The device of claim 1, further comprising:
a contrast solution compartment, wherein the contrast solution compartment is in fluid isolation from the wire channel, and wherein the contrast solution compartment includes at least one interior wall with volumetric gauge markings.

10. The device of claim 1, further comprising:
a flush compartment and a saline solution compartment, wherein the flush compartment and the saline solution compartment are in fluid isolation from each other and from other sections of the device.

11. The device of claim 1, wherein the one or more wall segments includes at least three wall segments with the at least one second flap extending from one of the at least three wall segments.

12. The device of claim 1, wherein the one or more wall segments form at least two gaps between the one or more wall segments.

13. The device of claim 1, wherein the inner is formed from a smooth, rigid material.

14. A device, comprising:
a basin that holds a liquid;
a wire containment section within the basin, the wire containment section including:
a wire channel accessible to the liquid,
an inner wall extending up from a bottom of the basin and forming an inner boundary of the wire channel,
a first flap extending orthogonally from the inner wall and over first portions of the wire channel,
one or more wall segments extending up from the bottom of the basin; the one or more wall segments forming a substantially circular outer boundary of the wire channel, and
a second flap extending orthogonally from the one or more wall segments and over second portions of the wire channel; and
a wire holder located outside of the wire containment section, the wire holder including multiple slots, each of the multiple slots being configured to hold an end portion of a wire,
wherein the wire containment section is configured to receive multiple coiled guidewires inserted below the first and second flaps into the wire channel so that the coiled guidewires expand against the one or more wall segments; and
wherein the wire containment section is further configured so that one end portion of each of the coiled guidewires extends through a gap in the one or more wall segments and is secured in the wire holder.

15. The device of claim 14, wherein pulling one of the end portions of one of the multiple coiled guidewires horizontally past the wire holder causes the one of the multiple coiled guidewires to tighten and slide against the inner wall.

16. The device of claim 15, further comprising:
an interior wall segment extending up from the base, the interior wall segment including an aperture sized to receive a diameterof any of the multiple coiled guidewires, wherein the aperture is located such that a direction of a pull on one of the guidewires, as it exits the wire channel, is substantially parallel to the base, when one of the end portions is threaded through the aperture.

17. The device of claim 14, wherein the one or more wall segments forms at least two gaps between the one or more wall segments.

18. The device of claim 14, further comprising:
a catheter channel surrounding the wire containment section and the wire holder, the catheter channel including at least one internal wall segment within the catheter channel, the at least one internal wall segment having various sized openings to hold tubing and catheters associated with a surgical procedure.

19. A method for using a storage tray associated with surgical procedures, the method comprising:
adding liquid into a basin of the storage tray, wherein the basin includes:
a horizontal base and a set of walls forming the basin,
a wire containment section within the basin; the wire containment section including a wire channel accessible to the liquid, an inner wall extending up from the base and forming an inner boundary of the wire channel, a first flap extending orthogonally from the inner wall and over first portions of the wire channel, one or more wall segments extending vertically from the base and forming an outer boundary of the wire channel, and a second flap extending orthogonally from the one or more wall segments and over second portions of the wire channel, and
a wire feed section within the basin and in fluid communication with the wire channel, the wire feed section including a wire holder with multiple slots, each of the multiple slots being configured to hold an end portion of a wire;
inserting multiple coiled guidewires below the first and second flaps into the wire channel so that the coiled guidewires expand against the one or more wall segments;
inserting an end portion of each of the multiple coiled guidewires into a different slot of the multiple slots;
selecting, as a selected guidewire, one of the multiple coiled guidewires for use during a surgical procedure;
removing the end portion of the selected guidewire from one of the multiple slots; and
pulling the end portion of the selected guidewire horizontally until the selected guidewire exits the wire channel.

20. The method of claim 19, further comprising:
inserting one or more catheters, into a catheter channel surrounding the wire containment section and the wire feed section, the catheter channel including a third flap extending orthogonally from the set of walls and above the catheter channel.

\* \* \* \* \*